(12) United States Patent
Saar et al.

(10) Patent No.: US 11,497,760 B2
(45) Date of Patent: Nov. 15, 2022

(54) METHOD FOR SOLUBILIZING POORLY WATER-SOLUBLE DIETARY SUPPLEMENTS AND PHARMACEUTICALLY ACTIVE AGENTS

(71) Applicant: ATHENION AG, Zug (CH)

(72) Inventors: Ingo Saar, Niederkassel (DE); Wolfgang Brysch, Berlin (DE); Jörg Von Wegerer, Berlin (DE)

(73) Assignee: Athenion AG, Zug (CH)

( * ) Notice: Subject to any disclaimer, the term of this patent is extended or adjusted under 35 U.S.C. 154(b) by 671 days.

(21) Appl. No.: 16/330,624

(22) PCT Filed: Aug. 30, 2017

(86) PCT No.: PCT/EP2017/001028
§ 371 (c)(1),
(2) Date: Mar. 5, 2019

(87) PCT Pub. No.: WO2018/046120
PCT Pub. Date: Mar. 15, 2018

(65) Prior Publication Data
US 2021/0205345 A1  Jul. 8, 2021

(30) Foreign Application Priority Data
Sep. 6, 2016  (EP) ..................... 16001941

(51) Int. Cl.
| | |
|---|---|
| A23L 33/12 | (2016.01) |
| A61K 31/7052 | (2006.01) |
| A23L 29/00 | (2016.01) |
| A23L 29/10 | (2016.01) |
| A23L 33/105 | (2016.01) |
| A23L 27/00 | (2016.01) |
| A61K 9/08 | (2006.01) |
| A61K 31/122 | (2006.01) |
| A61K 31/443 | (2006.01) |
| A61K 31/522 | (2006.01) |
| A61K 31/549 | (2006.01) |
| A61K 36/82 | (2006.01) |
| A61K 47/10 | (2017.01) |
| A61K 47/12 | (2006.01) |
| A61K 47/14 | (2017.01) |
| A61K 47/22 | (2006.01) |
| A61K 47/24 | (2006.01) |

(52) U.S. Cl.
CPC .......... *A61K 31/7052* (2013.01); *A23L 27/84* (2016.08); *A23L 29/035* (2016.08); *A23L 29/10* (2016.08); *A23L 33/105* (2016.08); *A23L 33/12* (2016.08); *A61K 9/08* (2013.01); *A61K 31/122* (2013.01); *A61K 31/443* (2013.01); *A61K 31/522* (2013.01); *A61K 31/549* (2013.01); *A61K 36/82* (2013.01); *A61K 47/10* (2013.01); *A61K 47/12* (2013.01); *A61K 47/14* (2013.01); *A61K 47/22* (2013.01); *A61K 47/24* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 6,300,377 B1 * | 10/2001 | Chopra | ................ | A61K 9/0095 514/458 |
| 6,441,050 B1 * | 8/2002 | Chopra | ................ | A61K 9/0095 424/439 |
| 6,761,903 B2 * | 7/2004 | Chen | .................... | A61K 9/4891 424/451 |
| 2008/0145411 A1 * | 6/2008 | Shinagawa | ............. | A23L 29/10 424/442 |
| 2009/0317532 A1 | 12/2009 | Bromley | | |
| 2021/0061771 A1 * | 3/2021 | Saar | ..................... | C07D 237/32 |

FOREIGN PATENT DOCUMENTS

| | | |
|---|---|---|
| CN | 101686924 A | 3/2010 |
| CN | 103536574 A | 1/2014 |
| EP | 1 591 020 A1 | 11/2005 |

OTHER PUBLICATIONS

International Search Report and Written Opinion dated Nov. 17, 2017 in corresponding International Application No. PCT/EP2017/001028.

* cited by examiner

*Primary Examiner* — Ralph J Gitomer
(74) *Attorney, Agent, or Firm* — Jon E. Gordon; Haug Partners LLP

(57) ABSTRACT

The present invention relates to a method for solubilizing poorly water-soluble dietary supplements and pharmaceutically active agents, to the solubilisate produced by this method and respective uses as a dietary supplement or pharmaceutical dosage form. A phosphatidylcholine-based solubilization method is disclosed.

7 Claims, No Drawings

METHOD FOR SOLUBILIZING POORLY WATER-SOLUBLE DIETARY SUPPLEMENTS AND PHARMACEUTICALLY ACTIVE AGENTS

CROSS-REFERENCE TO RELATED APPLICATIONS

This application is the National Stage entry under 35 U.S.C. § 371 of International Application No. PCT/EP2017/001028 filed on Aug. 30, 2017, published on Mar. 15, 2018 under Publication Number WO 2018/046120, which claims the benefit of priority under 35 U.S.C. § 119 of European Patent Application Number 16001941.0 filed Sep. 6, 2016, the entireties of which are herein incorporated by reference.

The present invention relates to a method for solubilizing poorly water-soluble dietary supplements and pharmaceutically active agents, to the solubilisate produced by this method and respective uses as a dietary supplement or pharmaceutical dosage form.

A broad variety of substances are known for which potentially beneficial effects on human health have been found in experimental settings. The use of many of them, however, has been seriously limited by the poor bioavailability that can be achieved by application forms known in the state-of-the-art. In pharmacology, bioavailability is a parameter that indicates the fraction of an administered dose of unchanged drug that finally becomes available in the systemic circulation for the desired pharmacological effects. Poor bioavailability is often due to a poor water solubility, respectively the lipophilic nature of the active agent to be administered. Hence, the use of such substances as a dietary supplement or as a pharmaceutically active agent is impaired when using standard dosage forms.

There is a variety of approaches for improving the solubility of such agents and in many cases also their bioavailability by using solubilization techniques. Herein the solubility of an agent in a medium is augmented by adding a third substance. These third substances are referred to as solubilizers (solubilizing agents), substances that may for example build a complex with the substance to be solubilized. Examples for such chelating agents are sodium benzoate and sodium salicylate. Another mechanism of action of solubilizers is the augmentation of the dissolving capacity of the solvent, for example by disturbing the cluster structure of water. Examples for such structure breakers are glycerol (glycerin) and macrogols (polyethylene glycol, PEG).

A third solubilization mechanism are micelle and liposome application technologies. They have won broad attention throughout the last decades. Herein the substance to be delivered is enclosed in a spherical aggregate of surfactant molecules. These molecules are characterized by a polar head group and a long nonpolar chain ("tail"). When given into an aqueous medium these molecules tend to associate by aggregating to spherical structures by orienting the polar head group towards the surrounding medium and the nonpolar chain towards the interior of the spheres. When these spheres consist of only one layer of such amphiphilic molecules they are referred to as micelles. Depending on the nature of the amphiphilic molecule and the reaction conditions it is also possible to form spheres with more than one layer. Herein a second layer is formed inside the outer layer of the sphere, the nonpolar groups of this second layer being oriented towards the nonpolar groups of the outer layer, and the polar head groups being oriented towards the interior of the sphere. Such aggregates are referred to as liposomes. In their structure they resemble the lipid bilayer of the cell membrane. There are also multi-layered liposomes in which at least two liposomal spheres are formed concentrically around one another, thus building a multispherical aggregate. When given in a lipophilic medium these substances tend to build inversed spherical structures where the lipophilic chain is oriented towards the solution medium and the other layers are arranged accordingly.

Different uses of such loaded spheres have been described in the art, among them the usage as a dosage form for the application of lipophilic substances and/or for increasing the bioavailability of the enclosed substance. In micelles, the enclosed nonpolar substance concentrates in the interior space of the sphere toward which the nonpolar chains of the amphiphilic molecules are oriented. In liposomes, however, the interior space of the spheres is an aqueous, respectively hydrophilic medium. It can serve for packaging hydrophilic molecules. Poorly water-soluble, respectively lipophilic molecules, however, gather mostly in between the lipophilic structures of the liposomal layers.

A micelle-based solubilisate for solubilizing dietary supplements is known for ubiquinone $Q_{10}$ (WO 03/007907 A1) or curcumin (WO2014/094921 A1). Therein an emulsifier with a HLB (hydrophilic-lipophilic balance) value of 9-16 or 13-18 is used, respectively. Polysorbate (Tween) 20 or 80 is preferred. Until now, the implementation of this technology is apparently limited to the production of chewing gum.

Polysorbates are widely used in these solubilization techniques. However, there is an ongoing controversy about a detrimental impact of polysorbates on health. Polysorbate-20 is discussed to be contaminated with unreacted 1,4-dioxane and ethylene oxide (at least from some suppliers). These are known skin-permeable carcinogenic substances (cf. FDA 1999, 21 CFR Part 173, Federal Register Vol 64, No. 104, pp. 29224-29227). Polysorbate-80 was recently found to have detrimental effects on murine gut microbiota, thus promoting obesity and inflammatory bowel diseases (Chassaing et al., Nature, 2015, 519, 92-96). A further problem of polysorbates such as Tween 80 is that they reduce the efficacy of widely used preservatives such as parabens by binding them (cf. Blanchard et al., Effect of sorbitol on interaction of phenolic preservatives with polysorbate 80, 1977, J Pharm Sci 66, p. 1470-1473). The paraben concentration, however, should not be increased accordingly because of their estrogenic potential (cf. Okubo et al.; ER-dependent estrogenic activity of parabens assessed by proliferation of human breast cancer MCF-7 cells and expression of ER-alpha and PR; 2001, Food Chem Toxicol 39, p. 1225-1232). Other well-known problems of polysorbates (in particular polysorbate 80) are hypersensitivity reactions of patients (cf. Steele et al., Hypersensitivity reactions to the polysorbate contained in recombinant erythropoietin and darbepoietin, Nephrology, 2005, 10, p. 317-320; Norris et al., Polysorbate 80 hypersensitivity reactions: a renewed call to action, Commun Oncol, 2010, 7, 425-428).

WO 2007/103435 A1 discloses that an increased bioavailability of curcuminoids (curcumin ester derivatives) can be achieved by admixing micelles, microemulsions or microencapsulated oils as well as an antioxidant and advisably a glucuronidation inhibitor to the curcuminoids. The use of a surfactant such as poloxamers or polysorbate 20, polysorbate 60, polysorbate 80 is particularly preferred. This composition shall be apt to treat Alzheimer's disease. Glucuronidation inhibitors, however, inhibit also the proper metabolization and consequently the elimination of other drugs or endogenous substances. Thus their use is a double-edged sword and should depend on the medication of each individual patient. Therefore such a composition might bear problems for an everyday use of a dietary supplement or a long-term medication.

From empirical pharmacokinetic measurements it is known that the organism can absorb micelles as well as liposomes in the gastrointestinal tract via the intestinal villi. However, their degree of absorption seems to be rather variable and therefore these methods have met a mixed success for augmenting the bioavailability of the enclosed compound. The transport, respectively the absorption rate over the cell membrane is an intrinsic characteristic for each substance, depending on a variety of factors such as molecule size, degree of lipophilicity and the presence of suitable transporter molecules inside the cell membrane. For many compounds these parameters are not known and would have to be determined first before finding a suitable packaging for this specific compound.

Liposomal applications have been widely discussed in medicine and pharmacology and some sophisticated solutions have been developed for specific active agents. Their use, however, is not very common. One reason are the relatively high production costs, another reason are possible adverse side effects. In particular, when parenterally applied, liposomes carry the risk of accumulating in the liver, the spleen and/or the bone marrow. Therefore, liposomal formulations are often viewed skeptically.

A nano-liposphere-based formulation method for increasing drug bioavailability was disclosed in WO 2013/108254. Although this method offers some advancement over the state-of-the-art there are also some inherent drawbacks. High-pressure homogenizers are needed for the production of these solid lipid nanoparticles. However, high-pressure induced drug degradation has been described for some drugs or dietary supplements. Lipid crystallization, gelation phenomena and co-existence of several colloidal species occur. Further restrictive factors such as cytotoxic effects after phagocytosis, toxic effects of organic residues and a difficult industrial scale-up have limited their use until now (Mehnert and Mader, Adv Drug Deliv Res 2001, 47, 165-196; Dudala et al., Int J Pharm Investg 2014, 4, 149-155). Moreover, their drug loading capacity is relatively small and they display a low viscosity. This makes them not very attractive for topic or transdermal application forms (Mukherjee et al., Indian J Pharm Sci 2009, 71, 349-358). Further, the use of an amphiphilic solvent such as lower alkyl esters of lactic acid or N-methylpyrrolidone is required in WO 2013/108254. N-methylpyrrolidone is listed as a substance of very high concern in respect of being potentially carcinogenic and toxic for reproduction, methyl lactate is usually hydrolyzed to lactate and methanol in an aqueous environment. Ethyl lactate etc. is well tolerated. However due to relatively high production costs it is not a very attractive solvent, particularly not for dietary supplements.

U.S. Pat. No. 6,441,050 B1 disclosed a method for generating an aqueous solution of Coenzyme Qi by means of a polysorbate surfactant, a triglyceride, a phospholipid, a sweetener and water.

The use of piperine as a chemosensitizing agent for a phospholipid-curcumin complex is revealed in EP 2228062 A1. An improvement of solubility is not addressed therein.

Another solubilization technique is the formation of inclusion complexes of the substance to be solubilized with cyclodextrins such as α-, β- or γ-cyclodextrin or cyclodextrin derivatives such as 2-hydroxypropyl-β-cyclodextrin, methyl-β-cyclodextrin or trimethyl-β-cyclodextrin. Typically, cyclodextrins are composed of 6 to 8 1,4-linked α-D-glucopyranosides forming macrocycles. Thus a water-soluble toroid (cone-shaped or bucket-shaped) structure is generated which is capable to host hydrophobic substances in its interior. The interior space is considerably less hydrophilic than the outside contacting the aqueous environment. Cyclodextrins are produced from starch by enzymatic treatment. They are loaded with the compound to be solubilized by dispersion. The compound to be solubilized can then be released by contacting these complexes with water, by pH or temperature changes, depending on the specific composition. However, the development of cyclodextrin is apparently not easy and relatively costly. This limited their use until now.

Nephrotoxicity problems have also been described for cyclodextrin-based formulations, when they become systemically available. However, the development of cyclodextrin formulations is apparently not easy and relatively costly. This limited their use until now (cf, Buschmann and Schollmeyer, J Cosmet Sci 2002, 53, 185-191; Numanoğlu et al., AAPS PharmSciTech 2007, 8, E1-E9; EP 0867175A1; WO 97/20861).

Wacker Chemie offers a cyclodextrin-based curcumin solubilisate with a 40 times increased bioavailability. This effect, however, is discussed controversially. It is supposed that it might be rather due to the concomitant use of Tween than to the cyclodextrin technology. As the health tolerance to Tween has been critically reviewed recently (see above), it might be preferable to use Tween-free solubilization techniques.

A method for enhancing the bioavailability of dosage forms of polar agents with a poor bioavailability that are administered in an enteric- or pH-sensitive coating is disclosed in AU 2014200052 A1. The problem is solved with a permeability enhancer such as glycerol and/or dimethylpalmityl-ammoniopropane sulfonate (PPS).

Thus, all these techniques have their advantages but also some drawbacks.

Therefore there is a need to provide an alternative method for solubilizing poorly water-soluble dietary supplements or pharmaceutically active agents. It should fulfil the following criteria:
- easy-to-handle
- no lengthy development time for finding a favorable composition
- no costly equipment needed
- inexpensive materials and production costs
- applicable for a broad range of poorly water-soluble dietary supplements or pharmaceutically active agents
- no addition of Tween (polysorbate) solubilizers needed.

Particularly for dietary supplements the development and production costs are a serious obstacle for developing suitable solubilization techniques, as the obtainable price on the market is limited.

Surprisingly, it was found that the method according to the invention is able to solve this task.

Herein, at least one dietary supplement or pharmaceutically active agent is solubilized by the method according to the invention, comprising the following steps:
a) Providing at least one pharmaceutically active agent or dietary supplement in the overall range of 0.5% to 25% per weight at room temperature and a pressure of 0.2 bar to 1 bar;
b) Adding in any sequence the solubilization agents of at least one phosphatidylcholine in the overall range of 20% to 80% per weight,
at least one medium-chained triglyceride in the overall range of 10% to 70% per weight, at least one lysophosphatidylcholine in the overall range of 1% to 15% per weight, at least one $C_2$ to $C_4$ alcohol in the overall range of 1% to 20% per weight, and at least one of glyceryl stearate and/or a saturated or unsaturated $C_{14}$ to $C_{20}$ fatty acid in the overall range of 0.5% to 10% per weight, respectively, wherein the relative weight percentages of all ingredients add up to 100% and all solubilization agents are independently from one another a food additive and/or a pharmaceutically acceptable excipient;

c) Cautiously heating the resulting mixture by continuously increasing the temperature with a continuous temperature increment of 0.5° C./min to 3° C./min over a period of 20 to 60 minutes;

d) Stopping the temperature increase in a temperature range of 30° C. to 125° C. as soon as a clear solution is reached; and e) Letting the resulting solubilisate cool down to room temperature.

Confusing and even contradictory definitions can be found in the art. In order to avoid any ambiguity a solubilisate according to the invention is defined as follows:

A solubilisate is the composition of the at least one substance to be solubilized and the solubilizing agents according to the invention. Further addition of a solvent or diluent shall not be covered by this term. The solubilisate according to the invention is produced first by a solubilization method according to the invention, then a specific nutritional or pharmaceutical composition is produced with said solubilisate, and finally said nutritional or pharmaceutical composition is packaged into a suitable container for the respective product.

It is characterized by the substantially complete solubilization of the substance, thus being a nearly perfect solution in which the molecules behave completely as independent entities in a solution and substantially undergo the distribution and thermodynamic rules of Brownian motion. Thus the solubilisate is a clear solution containing the respective dietary supplement or pharmaceutically active agent in a high concentration. In general, the solubilisate is not meant for intake without dilution. In most cases, a portioned solubilisate accounts to a volume of a few microliters.

In the scope of this patent application the terms "solubilization aggregate" or "solubilization essence" shall be used synonymously to "solubilisate".

A solubilisate according to the invention must be differentiated from a suspension (colloidal suspension). This term defines a heterogeneous mixture containing solid particles that sooner or later will undergo sedimentation. It is also different from an emulsion (a mixture of two liquids which usually are immiscible). For increasing the bioavailability and/or resorption of a substance the complete solubilization is highly preferably. Therefore solubilisates are preferred over suspensions or emulsions.

A solubilisate according to the invention must also be differentiated from a concentrate. A concentrate is a compound, respectively a composition of compounds without a diluent. Upon release of a concentrate into a diluent the concentrate dissolves itself either completely in the diluent or forms a suspension or emulsion with the diluent. A concentrate does not need the interaction with solubilizing agents, as it is intrinsically solvable in water or an aqueous solution.

The term solubilisate used according to the invention must be differentiated from the finished solution, respectively the prepared beverage to be imbibed. This finished solution according to the invention is generated by diluting the solubilisate according to the invention in a diluent, preferably an aqueous solution, in order to produce a beverage, respectively any fluid dosage form ready for intake by the consumer, respectively the patient.

A diluent in the scope of the present application is a diluting agent (dilutant, thinner). It is not part of the solubilisate according to the invention.

In the scope of the present application the term "solubilizing agent" refers to any chemical substance that is added to the dietary supplement or pharmaceutically active agent for solubilizing it so that the dietary supplement or pharmaceutically active agent can be solved thereupon in an aqueous solution. The term "solubilizer" shall be used synonymously.

In the scope of the present application the term "medicine" shall comprise human and veterinary medicine.

A great advantage of such a solubilisate consists in its small volume. Thus it can be easily portioned to patient- or consumer-friendly units, or relatively huge amounts of a solubilized substance can be shipped at low costs. In order to produce a finished solution the dilution of the solubilisate in an aqueous medium (e.g. tap water or mineral water) can be easily carried out by medical staff, patients or consumers. A further advantage of a solubilisate according to the invention is that it allows for a less cumbersome storage of oxidation-sensitive, light (incl. UV irradiation)-sensitive, heat-sensitive and/or moisture-sensitive dietary supplements and/or pharmaceutically active agents, as it requires a much lesser volume than the finished solution.

The method according to the invention is particularly suitable for the solubilization of lipophilic dietary supplements or pharmaceutically active agents. The most commonly used measure of lipophilicity is Log $P_{oct/wat}$, indicating the partition coefficient of a molecule between an aqueous and a lipophilic phase, usually water and 1-octanol. Eligible to be solubilized by the method of the invention are lipophilic dietary supplements or pharmaceutically active agents with Log P values ≥0, preferred ≥0.5, more preferred ≥1, still more preferred ≥1.5 and most preferred ≥2.

In a preferred embodiment of the method according to the invention the at least one pharmaceutically active agent or dietary supplement is provided in the overall range of 2% to 15% per weight of the solubilisate, in a more preferred embodiment in the overall range of 2% to 10% per weight of the solubilisate.

Phosphatidylcholines are a class of phospholipids linked to choline. They are a major component of cell membranes and are for example obtained from egg yolk, ox liver, marine animals, krill oil or soybeans. In practice, it showed that the origin of phosphatidylcholines influences their biological and chemical effects considerably. According to the invention the at least one phosphatidylcholine (PC) added as solubilization agent can be selected from the group comprising 1-palmitoyl-2-oleoyl-sn-glycero-3-phosphocholine (POPC), natural (non-hydrogenated) or hydrogenated soy bean PC, natural or hydrogenated egg PC, dipalmitoyl phosphatidylcholine (DPPC), dimyristoyl phosphatidylcholine (DMPC) or 1,2-dioleyl-SN-glycero-3-phosphocholine (DOPC), 1-oleoyl-palmitoyl phosphatidylcholine (OPPC), diasteroyl phosphatidylcholine (DSPC), monostearoylphosphatidylcholine (MSPC), diarachidoylphosphatidylcholine (DAPC), corn lecithin, cottonseed oil lecithin, rapeseed lecithin, phosphatidylethanolamine, phosphatidylserine, phosphatidylinositol, phosphatidylinositol polyphosphates, phosphatidylglycerol, phosphatidic acid, phosphatidylinositolamine, diphosphatidylglycerol (cardiolipin), sphingomyelin, ceramide aminoethylphosphonic acid, ceramide phosphorylglycerol, dicetylphosphoric acid, stearylamine, and mixtures thereof. Preferred phosphatidycholines are non-hydrogenated soybean PC, DMPC, POPC and DOPC. Particularly preferred is non-hydrogenated soybean PC.

Lecithin is commonly used as a synonym for phosphatidylcholines. It is a mixture of phosphatidylcholine and other compounds.

According to the method of the invention phosphatidylcholines are used in the overall range of 20% to 80% per weight of the solubilisate, preferred 40% to 70% per weight of the solubilisate, more preferred 50% to 65% per weight and most preferred 60% per weight of the solubilisate.

Medium-chained triglycerides (MCT) refer to triglycerides whose fatty acids have an aliphatic tail of 6-12 carbon atoms. Fatty acids incorporated in MCT are called medium-chain fatty acids (MCFA). In triglycerides three fatty acid molecules are bound to a glycerol backbone. Per definition, in MCT at least two of these three fatty acids must be MCFAs. According to the invention MCFA added as solubilization agent can be selected independently from one another from the group comprising caproic acid, enanthic acid, caprylic acid, pelargonic acid, capric acid, undecilyc acid, lauric acid, their unsaturated derivatives, and mixtures thereof. Preferred MCFA are caproic acid, caprylic acid, capric acid, and lauric acid.

It can be advantageous in some embodiments of the invention to use triglycerides containing 1 to 3 myristic acid and/or palmitic acid residues instead of MCFAs. Hence, these two fatty acids shall be subsumed under the term MCT according to the invention too.

MCT oils or MCT fats are oils or fats containing predominantly said MCT. These terms refer to a respective mixture of different MCT that may contain a variety of MCFA. According to the invention any reasonable mixing ratio shall be covered by these terms. MCT fats are often extracted from specific plant fats, while MCT oils do not occur naturally. MCT oils and MCT fats are broadly marketed as a healthy dietary supplement, respectively as a surrogate for long-chain fats in nutrition.

According to the method of the invention MCT are used in the overall range of 10% to 70% per weight of the solubilisate, preferred 20% to 40% per weight of the solubilisate, more preferred 25% to 35% per weight of the solubilisate and most preferred 30% per weight of the solubilisate.

Lysophosphatidylcholines (LPC, lysoPC, also: lysolecithins) are a class of derivatives of phosphatidylcholines, resulting of their partial hydrolysis in which one of the fatty acid groups is removed. In the organism this hydrolysis is effected by the enzyme phospholipase A2. According to the invention the at least one lysophosphatidylcholine added as solubilization agent can be selected independently from one another from the group comprising all hydrolyzed compounds of the phosphatidylcholines listed above, 1-lysophosphatidylcholines (2-acyl-sn-glycero-3-phosphocholines), 2-lysophosphatidylcholines, L-alpha-lysophosphatidylcholine, the respective lysoPC derivatives from natural lecithins such as soybean lecithin, egg-yolk lecithin, corn lecithin, cottonseed oil lecithin, and rapeseed lecithin, as well as phosphatidylethanolamine, phosphatidylserine, phosphatidylinositol, phosphatidylinositol polyphosphate, phosphatidylglycerol, phosphatidic acid, phosphatidylinositolamine, diphosphatidylglycerol (cardiolipin), and mixtures thereof.

According to the method of the invention lysophosphatidylcholines are used in the overall range of 1% to 15% per weight of the solubilisate, preferred 3% to 8% per weight of the solubilisate, more preferred 5% to 7% per weight of the solubilisate and most preferred 6% per weight of the solubilisate.

In the scope of the present application said lysophosphatidylcholines are not a mere variant or substitute for phosphatidylcholines but fulfill an independent role. Surprisingly, it was found that two solubilizing agents of similar but not identical chemical constitution can significantly improve the solubilizing effect, if used in an uneven ratio. According to the invention the ratio phosphatidylcholine to lysophosphatidylcholine is from 80:1 to 1.33:1, preferred 40:1 to 3:1, more preferred 25:1 to 5:1 and most preferred 20:1 to 8:1.

According to the invention the at least one $C_2$ to $C_4$ alcohol (lower alcohol) added as solubilization agent can be selected from the group comprising ethanol, propanol, isopropanol, butane-1-ol, butane-2-ol, isobutanol (2-methyl-1-propanol), ethylene glycol (ethane-1,2-diol), α-propylene glycol (propane-1,2-diol), 3-propylene glycol (propane-1-3-diol), 1,2-butylene glycol (butane-1,2-diol), 1,3-butylene glycol (butane-1,3-diol), 1,4-butylene glycol (butane-1,4-diol), and diethylene glycol. Preferred is ethanol.

According to the method of the invention $C_2$ to $C_4$ alcohols are used in the overall range of 1% to 20% per weight of the solubilisate, preferred 2% to 10% per weight of the solubilisate, more preferred 3% to 8% per weight of the solubilisate and most preferred 5% per weight of the solubilisate.

Glyceryl stearate (glycerol monostearate, GMS) is an emulsifier that helps to stabilize the oily components in the composition. The flaky powder is also hygroscopic. GMS is also used as thickening, emulsifying, anti-caking, anti-staling and preservative agent.

According to the invention the at least one saturated or unsaturated $C_{14}$ to $C_{20}$ fatty acid can be used instead of or in combination with glyceryl stearate. It can be selected from the group comprising myristic acid (14:0), pentadecanoic acid (15:0), palmitic acid (16:0), heptadecanoic acid (17:0), stearic acid (18:0), nonadecanoic acid (19:0), arachidic acid (20:0), myristoleic acid (14:1,cis-$\Delta^9$), palmitoleic acid (16:1, cis-$\Delta^9$), sapienic acid (16:1, cis-$\Delta^6$), hexadecatrienoic acid (16:3, (n-3)), oleic acid (18:1, cis-$\Delta^9$), elaidic acid (18:1, trans-$\Delta^9$), vaccenic acid (18:1, trans-$\Delta^1$), linoleic acid (18:2; cis,cis-$\Delta^9,\Delta^{12}$), linoleadic acid (18:2, trans,trans-$\Delta^9,\Delta^{12}$), α-linolenic acid (18:3, cis,cis,cis-$\Delta^9,\Delta^{12},\Delta^{15}$), ylinolenic acid (18:3, (ω-3)), calendic acid (8E,10E,12Z-octadecatrienoic acid), stearidonic acid (18:4 (n-3)), dihomo-γ-linolenic acid (20:3; (ω-6)), eicosadienoic acid (20:2, (n-6)), eicosatrienoic acid (20:3, (n-3)), eicosatetraenoic acid (20:4, (n-3)), arachidonic acid (20:4, cis,cis,cis,cis-$\Delta^5$, $\Delta^8,\Delta^{11},\Delta^{14}$), eicosapentaenoic acid (20:5, cis,cis,cis,cis,cis-$\Delta^5$, $\Delta^8,\Delta^{11}$, $\Delta^{14},\Delta^{17}$). Preferred are even-numbered $C_{14}$ to $C_{20}$ fatty acids. Particularly preferred is oleic acid.

According to the method of the invention glyceryl stearate and/or a saturated or unsaturated $C_{14}$ to $C_{20}$ fatty acid are used in the overall range of 0.5% to 10% per weight of the solubilisate, preferred 1% to 8% per weight of the solubilisate, more preferred 2% to 6% per weight of the solubilisate and most preferred 3% per weight of the solubilisate.

The method according to the invention is usually started at room temperature. However, in alternative embodiments it may be also possible to preheat either the at least one pharmaceutically active agent or dietary supplement or any of the solubilizing agents to be added in step b) of the inventive method, provided that the preheating temperature does not exceed 28° C.

The method according to the invention can be performed at a pressure of 0.2 bar to 1 bar. It is preferred, however, to run the method at 1 bar (atmospheric pressure). For certain applications it may be preferable to use a light vacuum. The technical equipment for applying, maintaining and controlling such a light vacuum is well known in the art.

According to the method of the invention the resulting mixture is cautiously heated in step c) by continuously increasing the temperature over a period of 20 to 60 minutes. In preferred embodiments this period is 25 to 40 minutes, and most preferred 30 to 35 minutes.

An essential feature of the method according to the invention is the temperature control (temperature increment per time and duration of the heating). While there is a variability in the relative amounts of the solubilizing agents the controlled temperature increase is essential. Apparently, there is an optimal window for each substance to be solubilized. The exact values are difficult to predict, they need to be found out empirically. It is assumed that there is also an interdependency with the selected solubilizing agents and their relative amounts.

The continuous temperature increment (the steepness of the temperature ramp) can vary between 0.5° C./min to 3° C./min, preferred 1° C./min to 2° C./min and most preferred 2° C./min.

According to step d) the temperature increase is stopped in a temperature range of 30° C. to 125° C. as soon as a clear solution is reached. This moment depends heavily on the selected dietary supplement or pharmaceutically active agent as well as on the selected solubilization agents and reaction conditions. Apparently, it is not possible to foretell this "solubilizing temperature" on the basis of the specific components that are going to be used. Each composition of these components displays specific characteristics which have to be found out experimentally. Thus it becomes to the experimenter to find out the optimal combination of these parameters.

It is understood that the method according to the invention can be varied in such a way that any of the solubilizing agents of step b) can be provided first and then the at least one dietary supplement or pharmaceutically active agent as well as the other solubilizing agents can be added in any sequence. It is also possible to provide a mixture of the solubilizing agents of step b) first and then add the at least one dietary supplement or pharmaceutically active agent. This variation was found to be neutral to the outcome of the method according to the invention.

In a preferred embodiment said mixture of the solubilizing agents of step b) and said at least one dietary supplement or pharmaceutically active agent are provided in a two-compartment system. This may facilitate the solubilization process according to the invention and each compartment can be marketed separately. For certain dietary supplements or pharmaceutically active agents this can be advantageous for the stability and thus for the shelf life of the solubilisate or the finished solution according to the invention.

The moment when the resulting solubilisate has become a clear solution is determined by observation of the experimenter. In general, this moment is achieved when the solution appears transparent and does not display any sedimentation, precipitation, slurs, smears or striping (zebra effect).

In an alternative embodiment the parameters for the temperature ramp according to the invention that have been determined as described before can be implemented in an automatized or half-automatized device setting. This may be advantageous, for example, in an upscale industrial application.

The solubilisates produced according to the method of the invention maintain this clearness upon cooling down and stay clear and stable upon being stored. The achievable storage time (roughly corresponding to the shelf life time of a product) is apparently not limited. In preliminary stability analyses there was no solubilisate according to the invention where the minimum storage time was less than 14 days. In some cases even a storage time of minimum 16 months could be assessed (see Exp. 6).

However, for augmenting the shelf life of solubilisates containing at least one oxidation-prone dietary supplement or pharmaceutically active agent at least one antioxidant can be added to the solubilisate. In preferred embodiments this at least one antioxidant is a food additive and/or a pharmaceutically acceptable excipient. Suitable antioxidants can be selected from the group comprising lactic acid, ascorbic acid, sodium ascorbate, calcium ascorbate, potassium ascorbate, fatty acid esters of ascorbic acid, ascorbyl palmitate, ascorbyl stearate, tocopherols, alpha-tocopherol, beta-tocopherol, gamma-tocopherol, delta-tocopherol, alpha-tocotrienol, beta-tocotrienol, gamma-tocotrienol, delta-tocotrienol, propyl gallate, octyl gallate, dodecyl gallate, ethyl gallate, guaiac resin, erythorbic acid, sodium erythorbate, erythorbin acid, sodium erythorbin, tert-butylhydroquinone, butylated hydroxyanisole, butylated hydroxytoluene, mono-, di-, trisodium phosphate, mono-, di-, tripotassium phosphate, anoxomer, ethoxyquin, potassium lactate, stannous chloride, sodium thiosulfate, 4-hexylresorcinol, glucose oxidase. Preferred are ascorbyl palmitate and alpha-tocopherol, beta-tocopherol, gamma-tocopherol, delta-tocopherol. Particularly preferred is a combination of ascorbyl palmitate and at least one of alpha-tocopherol, beta-tocopherol, gamma-tocopherol, delta-tocopherol.

According to the method of the invention this at least one antioxidant can be optionally added to said solubilisate or its preferred embodiments in the overall range of 0.01% to 10% per weight of the solubilisate, preferred 0.1% to 5% per weight of the solubilisate, more preferred 0.2% to 1% per weight of the solubilisate and most preferred 0.3% to 0.5% per weight of the solubilisate.

Thus the present application refers also to the solubilisate resulting from the solubilizing method according to the invention:

A solubilisate of at least one pharmaceutically active agent or dietary supplement, comprising: at least one pharmaceutically active agent and/or dietary supplement in the range of 0.5% to 25% per weight and the following solubilization agents:
  a) at least one phosphatidylcholine in the overall range of 20% to 80% per weight;
  b) at least one medium-chained triglyceride in the overall range of 10% to 70% per weight;
  c) at least one lysophosphatidylcholine in the overall range of 1% to 15% per weight;
  d) at least one $C_2$ to $C_4$ alcohol in the overall range of 1% to 20% per weight, and
  e) and at least one of glyceryl stearate or a saturated or unsaturated $C_{14}$ to $C_{20}$ fatty acid in the range of 0.5% to 10% per weight, respectively,
wherein the relative weight percentages of all ingredients add up to 100% and all solubilization agents are independently from one another a food additive and/or a pharmaceutically acceptable excipient.

In a preferred embodiment the solubilisate according to the invention comprises at least one pharmaceutically active agent and/or dietary supplement in the range of 2% to 15% per weight and
- a) at least one phosphatidylcholine in the overall range of 40% to 70% per weight;
- b) at least one medium-chained triglyceride in the overall range of 20% to 40% per weight;
- c) at least one lysophosphatidylcholine in the overall range of 3% to 8% per weight;
- d) at least one $C_2$ to $C_4$ alcohol in the overall range of 2% to 10% per weight, and
- e) and at least one of glyceryl stearate or a saturated or unsaturated $C_{14}$ to $C_{20}$ fatty acids in the range of 0.5% to 5% per weight, respectively, wherein the relative weight percentages of all ingredients add up to 100% and all solubilization agents are independently from one another a food additive and/or a pharmaceutically acceptable excipient.

In a further preferred embodiment the solubilisate according to the invention comprises at least one pharmaceutically active agent and/or dietary supplement in the range of 5% to 10% per weight and
- a) at least one phosphatidylcholine in the overall range of 40% to 60% per weight;
- b) at least one medium-chained triglyceride in the overall range of 25% to 35% per weight;
- c) at least one lysophosphatidylcholine in the overall range of 5% to 7% per weight;
- d) at least one $C_2$ to $C_4$ alcohol in the overall range of 4% to 7% per weight, and
- e) and at least one of glyceryl stearate or a saturated or unsaturated $C_{14}$ to $C_{20}$ fatty acids in the range of 0.5% to 5% per weight, respectively, wherein the relative weight percentages of all ingredients add up to 100% and all solubilization agents are independently from one another a food additive and/or a pharmaceutically acceptable excipient.

It showed that particularly good results could be obtained when glyceryl stearate is used in a method according to the invention, respectively comprised in a solubilisate according to the invention. Glyceryl stearate showed to be the best emulsifier to significantly reduce the turbidity of a solubilisate produced by a method according to the invention, respectively of a finished solution upon generating an aqueous solution from said solubilisate. Concomitantly, its refractive index is lowered. With the use of glyceryl stearate crystal clear solubilisates can be generated. This is a key factor for the appeal of dietary supplements on the market, respectively patient compliance for a drug with a pharmaceutically active agent that was solubilized this way. A further advantage of the use of glyceryl stearate is that upon storing a solubilisate of the invention over a longer period of time a crystallization of the solubilized substance in the solubilisate can be widely avoided. This is a major problem in many solubilization methods of the art. Thus this feature contributes to a longer shelf life of the solubilisates according to the invention.

For many dietary supplements and/or pharmaceutically active agents to be solubilized it showed that a combination of glyceryl stearate and oleic acid is particularly advantageous. There may be a synergism of the emulsifying potency of both substances.

Therefore the present application refers also to a solubilisate of at least one pharmaceutically active agent or dietary supplement, produced by a method according to the invention, wherein the solubilisate comprises glyceryl stearate.

The term food additive refers to substances that are added to food to preserve the flavor or enhance its taste and appearance. They bestow chemical, physical or physiological effects to the food for controlling its consistency, taste, color, chemical and microbiological durability, for regulating their practical and nutritional value or for ensuring efficient food production. They can be synthetic compounds or of natural origin. In virtually all countries they are strictly regulated. Each approved additive is assigned a unique number. In Europe this number is preceded by the prefix E.

According to the invention said solubilisate or its preferred embodiments may additionally contain an antioxidant as listed before in the overall range of 0.01% to 10% per weight, preferred 0.1% to 5% per weight, more preferred 0.2% to 1% per weight and most preferred 0.3% to 0.5% per weight.

In a particularly preferred embodiment of this solubilisate said at least one saturated or unsaturated $C_{14}$ to $C_{20}$ fatty acid is oleic acid.

In a particularly preferred embodiment of this solubilisate said at least one $C_2$ to $C_4$ alcohol is ethanol.

In preferred embodiments at least one antioxidant in the overall range of 0.01 to 10% per weight is added additionally in the solubilisate according to the invention in step b) of the method, wherein said at least one antioxidant is a food additive and/or a pharmaceutically acceptable excipient.

In particularly preferred embodiments said at least one antioxidant is ascorbyl palmitate and/or at least one tocopherol.

According to the invention a dietary supplement can be the compound to be solubilized. Thus all dietary supplements can be solubilized by the method according to the invention. The inventive method is particularly suitable for the solubilization of poorly water-soluble dietary supplements. Poor water solubility often coincides with a poor bioavailability. For dietary supplements, which are usually consumed orally, the term bioavailability defines the quantity or fraction of the ingested dose that is absorbed. Thus it is preferred that a dietary supplement having a poor bioavailability is used for the production of the solubilisate according to the invention. It is preferred that their bioavailability in application forms according to the state-of-the-art is less than 50%, more preferred less than 40%, more preferred less than 30%, even more preferred less than 20%, particularly preferred less than 15% and most preferred less than 10%.

Dietary supplements are defined as nutrients provided to a consumer that otherwise may not be consumed in a sufficient quantity. It also refers to compounds that may generally improve a person's health condition without being intended as a therapeutic means for a disease. Therefore different regulatory requirements exist for dietary supplements and pharmaceutical drugs in almost all countries. According to the invention, these dietary supplements shall be used exclusively for nutritional purposes in substantially healthy persons. Any possible therapeutic use in a patient in need thereof or double use shall not be covered by the term dietary supplement.

Often dietary supplements include not only one defined compound. They are provided in the form of plant extracts. Therefore in the scope of this patent application the term dietary supplements refers also to plant extracts intended for an exclusively dietary use.

Examples for compounds or plant extracts used as dietary supplements known to have a poor bioavailability are, without being limiting: Flavones, flavonols, flavon-3-ols, flavonones, flavonoids, resveratrol, turmeric, curcumin, curcuminoids, demethoxycurcumin, bisdemethoxycurcumin, bis-o-demethyl curcumin, quercetin, ellagic acid, naringenin, betulin, betulinic acid, folic acid (folate), ubiquinone (Q10, coenzyme Q), glutathione, eicosapentaenoic acid (EPA), docosahexaenoic acid (DHA), uridine, chromium dichloride, L-carnitine, ursolic acid, catechin, epicatechin, epigallocatechin (EGC), epigallocatechin gallate (EGCG), epicatechin gallate (ECG), polyphenols, berberin, melatonin, polydatin, isoflavones, liposoluble vitamins A (retinol, retinal), D, E (tocopherols), F, K, α- and β-keto-boswellic acid, L-tryptophan, 5-hydroxytryptophan, L-glycine, inositol, β-carotene, tocotrienols, ascorbyl palmitate, lecithin, lutein, luteolin, lycopene, zeaxanthin, β-cryptoxanthin, red clover, saw palmetto lipid extract, ω-3 fatty acids, steroidal terpenes, non-steroidal terpenes, terpenoids; saponins, sapogenins, diosgenin, *Dioscorea* spec. extract, *Dioscorea villosa* extract, protodioscin, *Tribulus terrestris* extract, essential oils, hypericin, xanthorhizol, pyrogallol, genistein, wogonin, morin, kaempferol, *Bacopa monneriextract*, bacopin, bacoside A, bacoside A3, bacoside B, xanthorhizol, ginseng extract, *Gingko biloba* extract, pycnogenol, capsaicin, *Rubia cordifolia* extract, *Lawsennia iermis* extract, Aloe vera extract, piperin, α-lipoic acid, bromelain, phlorizin, crocin, crocetin, bioperine, acerola, proanthocyanidins, anthocyanidins, aglycones of anthocyanins silibinin, silymarin, gingerols, ceramides, isoprene, prenol, isovaleric acid, geranyl pyrophosphate, eucalyptol, limonene, pinene, farnesyl pyrophosphate, artemisinin, bisabolol, geranylgeranyl pyrophosphate, phytol, taxol, forskolin, aphidicolin, squalene, lanosterol, oils, such as shark or other cartilaginous fish oils, vegetable oils, or oils from amaranth seed, rice, wheat germ or olives; squalenes, retinoids, tannins, cinnamic acid, lignins, as well as phytosterols such as β-sitosterol laurate ester, α-sitosterol laurate ester, γ-sitosterol laurate ester, campesterol myristearate ester, stigmasterol oleate ester, campesterol stearate ester, β-sitosterol oleate ester, β-sitosterol palmitate ester, β-sitosterol linoleate ester, α-sitosterol oleate ester, γ-sitosterol oleate ester, β-sitosterol myristearate ester, β-sitosterol ricinoleate ester, campesterol laurate ester, campesterol ricinoleate ester, campesterol oleate ester, campesterol linoleate ester, stigmasterol linoleate ester, stigmasterol laurate ester, stigmasterol caprate ester, α-sitosterol stearate ester, γ sitosterol stearate ester, α-sitosterol myristearate ester, γ-sitosterol palmitate ester, campesterol ricinoleate ester, stigmasterol ricinoleate ester, campesterol ricinoleate ester, α-sitosterol, β-sitosterol, γ-sitosterol, campesterol, stigmasterol, and stigmasterol stearate ester; extracts from adaptogenic plants such as Eleuterococcus senticosus (Siberian ginseng, eleuthero, ciwujia), *Rhodiola rosea* (rose root), *Schisandra chinensis* (five flavor berry), *Panax ginseng* (ginseng), *Gynostemma pentaphyllum* (Jiao Gu Lan), *Morinda citrifolia* (noni, Indian mulberry), *Lentinula edodes* (shiitake), *Ganoderma* spec. (reishi, lingzhi mushroom) such as *Ganoderma lucidum, Ganoderma tsugae* and *Ganoderma sichuanense, Grifola frondosa* (maitake mushroom, hen-of-the-woods), *Agaricus* spec. (almond mushroom) such as *Agaricus subrufescens* and *Agaricus blazei* Murill, *Withania somnifera* (ashwagandha, winter cherry), *Ocimum tenuiflorum* (tulsi, holy basil), *Lepidum meyenii* (maca), *Andrographis paniculata* (kalmegh), *Cannabis sativa* (marihuana), *Tabebuia impetiginosa* (lapacho), *Astragalus membranaceus* (astragalus, tragacanth).

In preferred embodiments bioperine (piperine, an extract from black pepper) can be added to further increase the bioavailability of the solubilized dietary supplement.

Thus the present application refers also to the solubilisate according to the invention for use in a dietary supplement preparation, wherein at least one dietary supplement is solubilized in said solubilisate.

According to the invention a pharmaceutically active agent (drug substance) can be the compound to be solubilized. The inventive method is particularly suitable for the solubilization of poorly water-soluble pharmaceutically active agents.

The internationally accepted BCS (Biopharmaceutical Classification System) classifies drug substances into four classes: Class 1 (high solubility—high permeability), Class 2 (low solubility—high permeability), Class 3 (high solubility—low permeability and Class 4 (low solubility—low permeability).

Herein the term solubility refers to the highest dose strength that is subject to an FDA biowaiver request. Herein, a drug is classified as highly soluble, when the highest dose strength is soluble in 250 ml or less of aqueous media over the pH range of 1-7.5. Correspondingly, drug substances that can't be solubilized that way are classified as poorly soluble.

Herein the term permeability refers to the extent of absorption of a drug in humans across the intestinal membrane (mucosa). According to the established definition a drug is classified as highly permeable if 90% or more of the orally administered dose are resorbed in the gastrointestinal tract. Correspondingly, a drug having an absorption rate of less than 90% is classified as low permeable.

Thus solubility and permeability are intrinsic substance properties. Resorption and bioavailability, however, describe pharmaceutic parameters that may be improved by suitable measures. Bioavailability is defined differently for pharmaceutically active agents. While resorption refers to the fraction from the orally applied substance amount that is absorbed from the gastrointestinal tract the bioavailability of a substance depends not only from resorption but also from species-specific protein binding in blood and from pharmacokinetic parameters such as first-pass metabolism.

According to a preferred embodiment of the invention pharmaceutical drugs having a poor solubility as defined above are used for the production of a solubilisate.

According to the invention it is preferred that pharmaceutical drugs having a poor permeability as defined above are used for the production of a solubilisate.

According to the invention it is particularly preferred that pharmaceutical drugs having a poor solubility as well as a poor permeability as defined above are used for the production of a solubilisate (Class 4 compounds).

Examples for Class 4 pharmaceutical drugs, without being limiting, are: acetaminophen (paracetamol), aciclovir, azathioprine, azithromycin, calcitriol, carisoprodol, cefdinir, cefixime, cefuroxime axetil, cephalexin, chlorothiazide, chlorthalidone, clarithromycin, cyclosporine, dapsone, dexamethasone, dronabinol, dutasteride, furosemide, glipizide, griseofulvin, hydrochlorothiazide, indinavir sulfate, isradipine, linezolid, loperamide, mebendazole, mercaptopurine, mesalamine, methylprednisolone, modafinil, nabumetone, nelfinavir mesylate, norelgestromin, nystatin, oxcarbazepine, oxycodone HCl, progesterone, pyrimethamine, ritonavir, spironolactone, sulfamethoxazole, trimethoprim, taladafil.

Thus, the present application refers also to a solubilisate according to the invention for use in a pharmaceutical dosage form, wherein at least one pharmaceutically active agent is solubilized in said solubilisate.

Moreover, the present application refers also to the use in medicine of the solubilisate according to the invention in a pharmaceutical dosage form. In a preferred embodiment said solubilisate comprises glyceryl stearate.

As laid out before, one goal of the solubilisate according to the invention is to enable an augmented resorption and/or bioavailability of the dietary supplement or pharmaceutically active agent solubilized in said solubilisate. Thus, the present application refers also to a solubilisate according to the invention, in which the solubilisate of the at least one dietary supplement and/or pharmaceutically active agent enhances the resorption and/or bioavailability of at least one of said dietary supplements or pharmaceutically active agents. In a preferred embodiment said solubilisate comprises glyceryl stearate.

A further aspect of the invention is that some pharmaceutical drugs or dietary supplements intrinsically have a bitter or unpleasant taste. In case of pharmaceutical drugs this may seriously impair patient compliance, in case of dietary supplements such a taste may be a serious commercialization obstacle. A solubilisate according to the invention can significantly help to mask this bitter or unpleasant taste and/or odor by caging the substance. The solubilisates according to the invention use to have a neutral taste, likewise the finished solutions containing a solubilisate according to the invention.

Thus the present invention relates to a method according to the invention, wherein the resulting solubilisate is used to mask a bitter or unpleasant taste and/or odor of the pharmaceutically active agent or dietary supplement.

Thus the present invention relates also to a solubilisate of a pharmaceutical drug or dietary supplement in which a bitter or unpleasant taste and/or odor of the pharmaceutical drug or dietary supplement is masked by the solubilisate prepared by the method according to the invention.

In a preferred embodiment said solubilisate of a pharmaceutical drug or dietary supplement used to mask a bitter or unpleasant taste and/or odor comprises glyceryl stearate.

Examples of pharmaceutical drugs with a bitter or unpleasant taste comprise, without being limiting, acetaminophen, albuterol, aminoguanidine hydrochloride, aminophylline, amitriptyline, amoxicillin trihydrate, ampicillin, amlodipine besylate, aspirin, azithromycin, barbiturates, berberin chloride, caffeine, calcium carbonate, calcium pantothenate, cephalosporins, cetirizine, chloramphenicol, chlordiazepoxide, chloroquine, chlorpheniramine, chlorpromazine, cimetidine, ciprofloxacin, clarithromycin, codeine, demerol, dextromethorphan, digitoxin, digoxin, diltiazem hydrochloride, diphenhydramine, diphenylhydantoin, doxazosin mesylate, doxylamine succinate, eletriptan, enoxacin, epinephrine, erythromycin, ethylefrine hydrochloride, etinidine, famotidine, fluconazole, glipizide, guaifenesin, ibuprofen, indeloxazine hydrochloride, lidocaine, lomotil, loratadine, lupitidine, magnesium oxide, meclizine, methacholine, morphine, neostigmine, nifentidine, niperotidine, nizatidine, ofloxacin, paracetamol, pefloxacin, penicillin, phenobarbital, phenothiazine, phenylbutazone, phenylpropanolamine, pipemidic acid, pirbuterol hydrochloride, piroxicam, prednisolone, propranolol hydrochloride, pseudoephedrine, pyridonecarboxylic acid antibacterials, ranitidine, roxatidine, salicylic acid, sertraline hydrochloride, sildenafil, spironolactone, sulbactam sodium, sulfonamides, sulfotidine, sulpyrine, sultamicillin tosylate, tenidap, terfenadine, theophylline, trimethoprim, tuvatidine, valdecoxib, zaltidine, and zonisamide.

In a preferred embodiment the solubilisate according to the invention contains a poorly soluble pharmaceutical agent with a bitter or unpleasant taste. In another preferred embodiment the solubilisate according to the invention contains a pharmaceutical agent with a low permeability having a bitter or unpleasant taste. In a particularly preferred embodiment the solubilisate according to the invention contains a BCS Class 4 pharmaceutical drug with a bitter or unpleasant taste. Suitable examples comprise acetaminophen (paracetamol), azithromycin, clarithromycin, glipizide and trimethoprim.

Many dietary supplements also have a bitter or unpleasant taste, in particular many phytochemicals such as alkaloids, tannins, phenolic or polyphenolic compounds, flavonoids, isoflavones, isoflavone glucosides, glucosinolates, isothiocyanates, cucurbitacins, oxygenated tetracyclic triterpenes.

In most cases, the solubilisate itself is not yet a dietary supplement preparation or pharmaceutical dosage form. To be ready for consumption, respectively intake the solubilisate is solved in a diluent. The preferred diluent for oral consumption or oral dosage forms is water. Therefor the solubilisate according to the invention is added to an aqueous solution in a suitable container. The container can be selected from a group comprising, but not limited to, bottles, flasks, vials, flacons, ampules, glasses, cups, drinking bowls, beverage cartons, Tetra Pak®, cans, canteens, mugs having a lid, steins having a lid, pouches, stand-up pouches, barrels, kegs, wineskins, hose-shaped containers and custom-built two- or multiple-compartment containers. Preferred containers are bottles, vials and beverage cartons.

It is preferred that the container with the aqueous solution and the solubilisate solved therein is shaken several times to ensure a homogeneous distribution of the solubilisate in the aqueous solution and by this way a uniform taste, a constant concentration, avoidance of slurs and an appealing presentation of the finished solution.

Thus the present application refers also to a finished solution, wherein a solubilisate according to the invention is solved in an aqueous solution.

Moreover, the present application refers also to a pharmaceutical composition containing at least one pharmaceutically active agent formulated in a solubilisate according to the invention or in a finished aqueous solution as defined before, and at least one pharmaceutically acceptable excipient.

The term "pharmaceutical excipients" refers to natural or synthetic compounds that are added to a pharmaceutical formulation alongside the pharmaceutical active agent. They may help to bulk up the formulation, to enhance the desired pharmacokinetic properties or the stability of the formulation, as well as be beneficial in the manufacturing process. Advantageous classes of excipients according to the invention include carriers, binding agents, lubricants, glidants, disintegrants, colorants, buffers, preservatives, emulsifiers, permeation enhancers, antioxidants, diluents, pH-regulators, fatliquors, solvents, consistency enhancers, hydrotropes, sweeteners, acidifiers, thickening agents, antiadherents, fillers, flavors, sweeteners, opacifiers, flavoring substances and aromatic substances.

It can be advantageous, respectively mandatory to add one or more pharmaceutically acceptable carrier to a pharmaceutically active agent. Eligible are all carriers known in the art and combinations thereof. In solid dosage forms they can be for example plant and animal fats, waxes, paraffins, starch, tragacanth, cellulose derivatives, polyethylene glycols, silicones, bentonites, silica, talcum, zinc oxide. For liquid dosage forms and emulsions suitable carriers are for example solvents, solubilizing agents, emulsifiers such as water, ethanol, isopropanol, ethyl carbonate, ethyl acetate, benzyl alcohol, benzyl benzoate, propylene glycol, 1,3-butyl glycol, cotton seed oil, peanut oil, olive oil, castor oil, sesame oil, glycerol fatty acid esters, polyethyl glycols, fatty acid esters of sorbitan. Suspensions according to the invention may use carriers known in the art such as diluents (e.g. water, ethanol or propylene glycol), ethoxylized isostearyl alcohols, polyoxyethylene and polyoxyethylene sorbitan esters, microcrystalline cellulose, bentonites, agar agar, tragacanth.

The term binding agents refers to substances that bind powders or glue them together, rendering them cohesive through granule formation. They serve as a "glue" of the formulation. Binding agents increase the cohesive strength of the provided diluent or filler.

Suitable binding agents are for example starch from wheat, corn, rice or potato, gelatine, naturally occurring sugars such as glucose, sucrose or beta-lactose, sweeteners from corn, natural and synthetic gums such as acacia, tragacanth or ammonium calcium alginate, sodium alginate, carboxymethyl cellulose, sodium carboxymethyl cellulose, hydroxypropyl carboxymethyl cellulose, polyethylene glycol, polyvinyl pyrrolidone, magnesium aluminum silicate, waxes and others. The percentage of the binding agent in the composition can range from 1-30% by weight, preferred 2-20% by weight, more preferred 3-10% by weight and most preferred 3-6% by weight.

In some embodiments it may be desirable that the prepared beverage generates some foam on being dissolved. Such an effect can be supported through the addition of a foaming agent that reduces the surface tension of the liquid, thus facilitating the formation of bubbles, or it increases its colloidal stability by inhibiting coalescence of bubbles. Alternatively, it may stabilize foam. Suitable examples include mineral oil, *quillaia* extract, triethyl citrate, sodium lauryl ether sulfate, sodium lauryl sulfate, ammonium lauryl sulfate.

Alternatively, some solubilisates according to the invention may appear slightly foamy upon preparation. Though this does not interfere with the desired application it may affect patient compliance in case of a medication or the commercial success in case of dietary supplements. Therefore it may be desirable to add a pharmaceutically or nutritionally acceptable anti-foaming agent (defoamer) to the solubilisate. Examples are polydimethylsiloxane or silicone oil in dietary supplements or simethicone in pharmaceuticals.

Colorants are excipients that bestow a colorization to the composition of the drink, respectively the dosage form. These excipients can be food colorants. They can be adsorbed on a suitable adsorption means such as clay or aluminum oxide. The amount of the colorant may vary between 0.01 and 10% per weight of the composition, preferred between 0.05 and 6% per weight, more preferred between 0.1 and 4% per weight, most preferred between 0.1 and 1% per weight.

Suitable food or pharmaceutical colorants are for example curcumin, riboflavin, riboflavin-5'-phosphate, tartrazine, alkannin, quinolione yellow WS, Fast Yellow AB, riboflavin-5'-sodium phosphate, yellow 2G, Sunset yellow FCF, orange GGN, cochineal, carminic acid, citrus red 2, carmoisine, amaranth, Ponceau 4R, Ponceau SX, Ponceau 6R, erythrosine, red 2G, Allura red AC, Indathrene blue RS, Patent blue V, indigo carmine, Brilliant blue FCF, chlorophylls and chlorophyllins, copper complexes of chlorophylls and chlorophyllins, Green S, Fast Green FCF, Plain caramel, Caustic sulphite caramel, ammonia caramel, sulphite ammonia caramel, Black PN, Carbon black, vegetable carbon, Brown FK, Brown HT, alpha-carotene, beta-carotene, gamma-carotene, annatto, bixin, norbixin, paprika oleoresin, capsanthin, capsorubin, lycopene, beta-apo-8'-carotenal, ethyl ester of beta-apo-8'-carotenic acid, flavoxanthin, lutein, cryptoxanthin, rubixanthin, violaxanthin, rhodoxanthin, canthaxanthin, zeaxanthin, citranaxanthin, astaxanthin, betanin, anthocyanins, saffron, calcium carbonate, titanium dioxide, iron oxides, iron hydroxides, aluminum, silver, gold, pigment rubine, tannin, orcein, ferrous gluconate, ferrous lactate.

Flavor enhancers are widely used for food and drinks. Suitable examples are glutamic acid, monosodium glutamate, monopotassium glutamate, calcium diglutamate, monoammonium glutamate, magnesium diglutamate, guanylic acid, sodium guanylate, disodium guanylate, dipotassium guanylate, calcium guanylate, inosinic acid, disodium inosinate, dipotassium inosinate, calcium inosinate, calcium 5'-ribonucleotides, disodium 5'-ribonucleotides, glycine, sodium glycinate, zinc acetate, gum benzoic, thaumatin, glycyrrhizin, neohesperidine dihydrochalcone, glyceryl monoacetate, glyceryl diacetate.

Moreover, buffer solutions are preferred for liquid formulations, in particular for pharmaceutical liquid formulations. The terms buffer, buffer system and buffer solution, in particular of an aqueous solution, refer to the capacity of the system to resist a pH change by the addition of an acid or a base, or by dilution with a solvent. Preferred buffer systems may be selected from the group comprising formate, lactate, benzoic acid, oxalate, fumarate, aniline, acetate buffer, citrate buffer, glutamate buffer, phosphate buffer, succinate, pyridine, phthalate, histidine, MES (2-(N-morpholino) ethanesulfonic acid, maleic acid, cacodylate (dimethyl arsenate), carbonic acid, ADA (N-(2-acetamido)imino diacetic acid, PIPES (4-piperazine-bis-ethanesulfonic acid), BIS-TRIS propane (1,3-bis[tris(hydroxymethyl)mehylaminol] propane), ethylene diamine, ACES (2-[(amino-2-oxoethyl) amino]ethanesulfonic acid), imidazol, MOPS (3-(N-morphino)-propanesulfonic acid, diethyl malonic acid, TES (2-[tris(hydroxymethyl)methyl]aminoethanesulfonic acid, HEPES (N-2-hydroxyethylpiperazine-N'-2-ethanesulfonic acid), as well as other buffers with a pKa between 3.8 and 7.7.

Preferred are carbonic acid buffers such as acetate buffer and dicarboxylic acid buffers such as fumarate, tartrate and phthalate as well as tricarboxylic acid buffers such as citrate.

A further group of preferred buffers are inorganic buffers such as sulfate hydroxide, borate hydroxide, carbonate hydroxide, oxalate hydroxide, calcium hydroxide and phosphate buffers. Another group of preferred buffers are nitrogen-containing puffers such as imidazol, diethylene diamine and piperazine. Furthermore preferred are sulfonic acid buffers such as TES, HEPES, ACES, PIPES, [(2-hydroxy-1,1-bis-(hydroxymethyl)ethyl)amino]-1-propanesulfonic acid (TAPS), 4-(2-hydroxyethyl)piperazine-1-propanesulfonic acid (EEPS), 4-morpholino-propanesulfonic acid (MOPS) and N,N-bis-(2-hydroxyethyl)-2-aminoethanesulfonic acid (BES). Another group of preferred buffers are glycine, glycyl-glycine, glycyl-glycyl-glycine, N,N-bis-(2-hydroxyethyl)glycine and N-[2-hydroxy-1,1-bis(hydroxymethyl)ethyl]glycine (tricine). Preferred are also amino acid buffers such as glycine, alanine, valine, leucine, isoleucine, serine, threonine, phenylalanine, tyrosine, tryptophan, lysine, arginine, histidine, aspartate, glutamate, asparagine, glutamine, cysteine, methionine, proline, 4-hydroxy proline, N,N,N-trimethyllysine, 3-methyl histidine, 5-hydroxy-lysine, o-phosphoserine, gamma-carboxyglutamate, [epsilon]-N-acetyl lysine, [omega]-N-methyl arginine, citrulline, ornithine and their derivatives.

Preservatives for liquid dosage forms or supplements can be used on demand. They may be selected from the group comprising, but not limited to, sorbic acid, potassium sorbate, sodium sorbate, calcium sorbate, methyl paraben, ethyl paraben, methyl ethyl paraben, propyl paraben, benzoic acid, sodium benzoate, potassium benzoate, calcium benzoate, heptyl p-hydroxybenzoate, sodium methyl para-hydroxybenzoate, sodium ethyl para-hydroxybenzoate, sodium propyl para-hydroxybenzoate, benzyl alcohol, benzalkonium chloride, phenylethyl alcohols, cresols, cetylpyridinium chloride, chlorobutanol, thiomersal (sodium 2-(ethylmercurithio) benzoic acid), sulfur dioxide, sodium sulphite, sodium bisulphite, sodium metabisulphite, potassium metabisulphite, potassium sulphite, calcium sulphite, calcium hydrogen sulphite, potassium hydrogen sulphite, biphenyl, orthophenyl phenol, sodium orthophenyl phenol, thiabendazole, nisin, natamycin, formic acid, sodium formate, calcium formate, hexamine, formaldehyde, dimethyl dicarbonate, potassium nitrite, sodium nitrite, sodium nitrate, potassium nitrate, acetic acid, potassium acetate, sodium acetate, sodium diacetate, calcium acetate, ammonium acetate, dehydroacetic acid, sodium dehydroacetate, lactic acid, propionic acid, sodium propionate, calcium propionate, potassium propionate, boric acid, sodium tetraborate, carbon dioxide, malic acid, fumaric acid, lysozyme, copper-(II)-sulfate, chlorine, chlorine dioxide and other suitable substances or compositions known to the person skilled in the art.

Additional emulsifiers can be selected for example from the following anionic and non-ionic emulsifiers: Anionic emulsifier waxes, cetyl alcohol, cetylstearyl alcohol, stearic acid, oleic acid, polyoxyethylene polyoxypropylene block polymers, addition products of 2 to 60 mol ethylene oxide to castor oil and/or hardened castor oil, wool wax oil (lanolin), sorbitan esters, polyoxyethylene alkyl esters, polyoxyethylene sorbitan fatty acid esters, polyoxyethene sorbitan monolaurate, polyoxyethene sorbitan monooleate, polyoxyethene sorbitan monopalmitate, polyoxyethene sorbitan monostearate, polyoxyethene sorbitan tristearate, polyoxyethene stearate, polyvinyl alcohol, metatartaric acid, calcium tartrate, alginic acid, sodium alginate, potassium alginate, ammonium alginate, calcium alginate, propane-1,2-diol alginate, carrageenan, processed eucheuma seaweed, locust bean gum, tragacanth, acacia gum, karaya gum, gellan gum, gum ghatti, glucomannane, pectin, amidated pectin, ammonium phosphatides, brominated vegetable oil, sucrose acetate isobutyrate, glycerol esters of wood rosins, disodium phosphate, trisodium diphosphate, tetrasodium diphosphate, dicalcium diphosphate, calcium dihydrogen diphosphate, sodium triphosphate, pentapotassium triphosphate, sodium polyphosphates, sodium calcium polyphosphate, calcium polyphosphates, ammonium polyphosphate, beta-cyclodextrin, powdered cellulose, methyl cellulose, ethyl cellulose, hydroxypropyl cellulose, hydroxypropyl methylcellulose, ethyl methyl cellulose, carboxymethyl cellulose, sodium carboxymethyl cellulose, ethyl hydroxyethyl cellulose, croscarmellose, enzymically hydrolyzed carboxymethyl cellulose, mono- and diglycerides of fatty acids, glyceryl monostearate, glyceryl distearate, acetic acid esters of mono- and diglycerides of fatty acids, lactic acid esters of mono- and diglycerides of fatty acids, citric acid esters of mono- and diglycerides of fatty acids, tartaric acid esters of mono- and diglycerides of fatty acids, mono- and diacetyl tartaric acid esters of mono- and diglycerides of fatty acids, mixed acetic and tartaric acid esters of mono- and diglycerides of fatty acids, succinylated monoglycerides, sucrose esters of fatty acids, sucroglycerides, polyglycerol esters of fatty acids, polyglycerol polyricinoleate, propane-1,2-diol esters of fatty acids, propylene glycol esters of fatty acids, lactylated fatty acid esters of glycerol and propane-1, thermally oxidized soy bean oil interacted with mono- and diglycerides of fatty acids, dioctyl sodium sulphosuccinate, sodium stearoyl-2-lactylate, calcium stearoyl-2-lactylate, stearyl tartrate, stearyl citrate, sodium stearoyl fumarate, calcium stearoyl fumarate, stearyl tartrate, stearyl citrate, sodium stearoyl fumarate, calcium stearoyl fumarate, sodium laurylsulfate, ethoxylated mono- and diglycerides, methyl glucoside-coconut oil ester, sorbitan monostearate, sorbitan tristrearate, sorbitan monolaurate, sorbitan monooleate, sorbitan monopalmitate, sorbitan trioleate, calcium sodium polyphosphate, calcium polyphosphate, ammonium polyphosphate, cholic acid, choline salts, distarch glycerol, starch sodium octenyl succinate, acetylated oxidized starch.

Preferred are glycerin monooleate and stearic acid.

Stabilizers are substances that can be added to prevent unwanted changes. Though stabilizers are not real emulsifiers they may also contribute to the stability of emulsions, respectively solubilisates. Suitable examples for stabilizers are oxystearin, xanthan gum, agar, oat gum, guar gum, tara gum, polyoxyethene stearate, aspartame-acesulfame salt, amylase, proteases, papain, bromelain, ficin, invertase, polydextrose, polyvinyl pyrrolidone, polyvinyl polypyrrolidone, triethyl citrate, maltitol, maltitol syrup.

Suitable as additional surface-active solubilizing agents (solubilizers) are for example diethylene glycol monoethyl ester, polyethyl propylene glycol co-polymers, cyclodextrins such as α- and β-cyclodextrin, glyceryl monostearates such as Solutol HS 15 (Macrogol-15-hydroxystearate from BASF, PEG 660-15 hydroxystearates), sorbitan esters, polyoxyethylene glycol, polyoxyethylene sorbitanic acid esters, polyoxyethylene sorbitan monooleate, polyoxyethylene oxystearic acid triglyceride, polyvinyl alcohol, sodium dodecyl sulfate, (anionic) glyceryl monooleates etc.

Suitable aromatic and flavoring substances comprise above all essential oil that can be used for this purpose. In general, this term refers to volatile extracts from plants or parts of plants with the respective characteristic smell. They can be extracted from plants or parts of plants by steam distillation.

Examples are: Essential oils, respectively aromatic substances from sage, cloves, chamomile, anise, star anise, thyme, tea tree, peppermint, mint oil, menthol, cineol, eucalyptus oil, mango, figs, lavender oil, chamomile blossoms, pine needles, cypress, oranges, rosewood, plum, currant, cherry, birch leaves, cinnamon, limes, grapefruit, tangerine, juniper, valerian, lemon balm, lemon grass, palmarosa, cranberry, pomegranate, rosemary, ginger, pineapple, guava, echinacea, ivy leave extract, blueberry, kaki, melons etc. or mixtures thereof, as well as mixtures of menthol, peppermint and star anise oil or menthol and cherry flavor.

These aromatic or flavoring substances can be included in the range of 0.0001 to 10% per weight (particularly in a composition), preferred 0.001 to 6% per weight, more preferred 0.001 to 4% per weight, most preferred 0.01 to 1% per weight, with regard to the total composition. Application- or single case-related it may be advantageous to use differing quantities.

Suitable sweeteners can be selected from the group comprising, but not limited to, mannitol, glycerol, acesulfame potassium, aspartame, cyclamate, isomalt, isomaltitol, saccharin and its sodium, potassium and calcium salts, sucralose, alitame, thaumatin, glycyrrhizin, neohesperidine dihydrochalcone, steviol glycosides, neotame, aspartame-acesulfame salt, maltitol, maltitol syrup, lactitol, xylitol, erythritol.

Suitable additional solvents may be selected from the group comprising, but not limited to, water, carbonated water, water for injection, water with isotonizing agents, saline, isotonic saline, alcohols, particularly ethyl and n-butyl alcohol, glycols, oleic and linoleic acid triglycerides, caprylic and capric acid mono-, di- and triglycerides, polyoxyethylene caprylic and capric acid glycerides, propylene glycol fatty acid esters, low alkyl fatty acid esters, soy bean oil, propylene glycol laurate, polyoxyethylene (35) castor oil, polyoxyethylene glyceryl trioleate, ethyl butyrate, ethyl caprylate, ethyl oleate and mixtures thereof.

Suitable isotonizing agents are for example pharmaceutically acceptable salts, in particular sodium chloride and potassium chloride, sugars such as glucose or lactose, sugar alcohols such as mannitol and sorbitol, citrate, phosphate, borate and mixtures thereof.

Suitable thickening agents can be selected from the group comprising, but not limited to, polyvinyl pyrrolidone, methyl cellulose, hydroxypropyl methyl cellulose, hydroxypropyl cellulose, dextrins, polydextrose, modified starch, alkaline modified starch, bleached starch, oxidized starch, enzyme-treated starch, monostarch phosphate, distarch phosphate esterified with sodium trimetaphosphate or phosphorus oxychloride, phosphate distarch phosphate, acetylated distarch phosphate, starch acetate esterified with acetic anhydride, starch acetate esterified with vinyl acetate, acetylated distarch adipate, acetylated distarch glycerol, distarch glycerin, hydroxypropyl starch, hydroxy propyl distarch glycerin, hydroxypropyl distarch phosphate, hydroxypropyl distarch glycerol, starch sodium octenyl succinate, acetylated oxidized starch, hydroxyethyl cellulose.

Diluents or fillers are inactive substances added to drugs in order to handle minimal amounts of active agents. They can be useful in the solubilizing process. Examples for suitable diluents are water, mannitol, pre-gelatinized starch, starch, microcrystalline cellulose, powdered cellulose, silicified microcrystalline cellulose, dibasic calcium phosphate dihydrate, calcium phosphate, calcium carbonate, hydroxypropyl cellulose, hydroxyethyl cellulose, hydroxypropyl methylcellulose, polyethylene glycol, xanthum gum, gum arabic or any combination thereof.

Opacifiers are substances that render the drinkable liquid opaque, if desired. They must have a refractive index substantially different from the solvent, in most cases here water. At the same time they should be inert to the other components of the composition. Suitable examples include titanium dioxide, talc, calcium carbonate, behenic acid, cetyl alcohol, or mixtures thereof.

According to the invention all of the aforementioned excipients and classes of excipients can be used without limitation alone or in any conceivable combination thereof, as long as the inventive use of a solubilisate is not thwarted, toxic actions may occur or the respective national legislations are infracted.

Thus the present application refers also to a pharmaceutical composition according to the invention for use in medicine.

In preferred embodiments the pharmaceutical composition according to the invention comprises at least one pharmaceutically active agent, wherein said at least one pharmaceutically active agents is a BCS Class 4 pharmaceutically active agent.

In particular preferred embodiments the pharmaceutical composition according to the invention comprises at least one pharmaceutically active agent, wherein said at least one pharmaceutically active agents is a BCS Class 4 pharmaceutically active agent selected from a group consisting of acetaminophen, aciclovir, azathioprine, azithromycin, calcitriol, carisoprodol, cefdinir, cefixime, cefuroxime axetil, cephalexin, chlorothiazide, chlorthalidone, clarithromycin, cyclosporine, dapsone, dexamethasone, dronabinol, dutasteride, furosemide, glipizide, griseofulvin, hydrochlorothiazide, indinavir sulfate, isradipine, linezolid, loperamide, mebendazole, mercaptopurine, mesalamine, methylprednisolone, modafinil, nabumetone, nelfinavir mesylate, norelgestromin, nystatin, oxcarbazepine, oxycodone HCl, progesterone, pyrimethamine, ritonavir, spironolactone, sulfamethoxazole, trimethoprim and taladafil.

The aforementioned solubilisates of dietary supplements alone or in combination can be combined with a variety of additives, as laid out in the following:

Suitable vitamins are for example vitamin C (L-ascorbic acid, sodium L-ascorbate, calcium L-ascorbate, potassium L-ascorbate, L-ascorbyl 6-palmitate), vitamin A (retinol, retinyl acetate, retinyl palmitate, beta-carotene), vitamin D (cholecalciferol, ergocalciferol), vitamin E (D-alpha-tocopherol, DL-alpha-tocopherol, D-alpha-tocopheryl acetate, DL-alpha-tocopheryl acetate, D-alpha-tocopheryl succinate), vitamin K (phylloquinone), vitamin B1 (thiamin hydrochloride, thiamin mononitrate), vitamin B2 (riboflavin, sodium riboflavin 5'-phosphate), niacin (nicotinic acid, nicotinamide), pantothenic acid (calcium D-pantothenate, sodium D-pantothenate, D-panthenol), vitamin B6 (pyridoxine hydrochloride, pyridoxine 5'-phosphate), folic acid (pteroyl monoglutaminic acid), vitamin B12 (cyanocobalamin, hydroxocobalamin), biotin (D-biotin).

Suitable minerals to be included are for example calcium (calcium carbonate, calcium chloride, citric acid calcium salt, calcium gluconate, calcium glycerophosphate, calcium lactate, ortho-phosphoric acid calcium salt, calcium hydroxide, calcium oxide), magnesium (magnesium acetate, magnesium carbonate, magnesium chloride, citric acid magnesium salt, magnesium gluconate, magnesium glycerophosphate, ortho-phosphoric acid magnesium salt, magnesium lactate, magnesium hydroxide, magnesium oxide, magnesium sulfate), iron (iron carbonate, iron citrate, iron ammonium citrate, iron gluconate, iron fumarate, iron sodium diphosphate, iron lactate, iron sulfate, iron diphosphate, ferric saccharate, elemental iron), copper (copper carbonate, copper citrate, copper gluconate, copper sulfate, copper lysine complex), iodine (sodium iodide, sodium iodate, potassium iodide, potassium iodate), zinc (zinc acetate, zinc chloride, zinc citrate, zinc gluconate, zinc lactate, zinc oxide, zinc carbonate, zinc sulfate), manganese (manganese carbonate, manganese chloride, manganese citrate, manganese gluconate, manganese glycerophosphate, manganese sulfate), sodium (sodium bicarbonate, sodium carbonate, sodium chloride, sodium citrate, sodium gluconate, sodium lactate, sodium hydroxide, ortho-phosphoric acid sodium salt), potassium (potassium bicarbonate, potassium carbonate, potassium chloride, potassium citrate, potassium gluconate, potassium glycerophosphate, potassium lactate, potassium hydroxide, ortho-phosphoric acid potassium salt), selenium (sodium selenite, sodium hydrogen selenite, sodium selenite), chrome (chrome-(I)-chloride, chrome-(III)-sulfate), molybdenum (ammonium molybdate (molybdenum (VI), sodium molybdate (molybdenum (VI)), fluorine (sodium fluoride, potassium fluoride), chlorine, phosphor.

Trace elements are dietary minerals that are needed by the organism in very small amounts for growth, development and physiology, for example as co-enzymes. Some of them are virtually always present in the organism in sufficient quantities, others have to be substituted in persons in need thereof. They can be selected from the group comprising, but not limited to, chrome, cobalt, iron, iodine, copper, manganese, molybdenum, selenium, zinc, fluoride, silicon, arsenic, nickel, rubidium, tin, vanadium. They can be substituted either as a pure element or in any of the mineral forms mentioned above.

Stimulants are often and worldwide used in drinks. According to the World Health Organization (WHO) this term refers to any kind of substances increasing, accelerating or improving neuronal activity. These substances have often a psychomimetic effect. Most popular stimulants include xanthines such as caffeine, theophylline and theobromine. Guaraná contains the aforementioned xanthines. A further popular stimulant is nicotine, respectively nicotinic acid. However, there is a broad group of stimulants that in many countries are banned by law, expected to be banned in the near future, or underlie a strict regulation of health authorities, needing the prescription of a physician. This is due to their dependence potential and other hazards to consumers' health, attention deficits in traffic etc., or negative effects on social life. This group includes a.o. amphetamine and its derivatives, a group of piperazine derivatives, cocaine and drugs for the treatment of narcolepsy and attention deficit hyperactivity disorder (ADHD). Hence the use of this group of substances according to the invention may be possible, but is discouraged, if legally banned. Preferred is the use of caffeine.

Further suitable antioxidants can be selected from the group comprising lactic acid, ascorbic acid, sodium ascorbate, calcium ascorbate, potassium ascorbate, fatty acid esters of ascorbic acid, ascorbyl palmitate, ascorbyl stearate, tocopherols, alpha-tocopherol, gamma-tocopherol, delta-tocopherol, propyl gallate, octyl gallate, dodecyl gallate, ethyl gallate, guaiac resin, erythorbic acid, sodium erythorbate, erythorbin acid, sodium erythorbin, tert-butylhydroquinone, butylated hydroxyanisole, butylated hydroxytoluene, mono-, di-, trisodium phosphate, mono-, di-, tripotassium phosphate, anoxomer, ethoxyquin, potassium lactate, stannous chloride, sodium thiosulfate, 4-hexylresorcinol, glucose oxidase.

The term tocopherol refers to any of the aforementioned tocopherols or a mixture thereof.

Suitable acidity regulators can be selected from the group comprising acetic acid, potassium acetate, sodium acetate, sodium diacetate, calcium acetate, carbon dioxide, malic acid, fumaric acid, sodium lactate, potassium lactate, calcium lactate, ammonium lactate, magnesium lactate, citric acid, mono-, di-, trisodium citrate, mono-, di-, tripotassium citrate, mono-, di-, tricalcium citrate, tartaric acid, mono-, disodium tartrate, mono-, dipotassium tartrate, sodium potassium tartrate, ortho-phosphoric acid, lecithin citrate, magnesium citrate, ammonium malate, sodium malate, sodium hydrogen malate, calcium malate, calcium hydrogen malate, adipic acid, sodium adipate, potassium adipate, ammonium adipate, succinic acid, sodium fumarate, potassium fumarate, calcium fumarate, ammonium fumarate, 1,4-heptonolactone, triammonium citrate, ammonium ferric citrate, calcium glycerophosphate, isopropyl citrate, potassium carbonate, potassium bicarbonate, ammonium carbonate, ammonium bicarbonate, magnesium carbonate, magnesium bicarbonate, ferrous carbonate, ammonium sulfate, aluminum potassium sulfate, aluminum ammonium sulfate, sodium hydroxide, potassium hydroxide, ammonium hydroxide, magnesium hydroxide, gluconic acid.

Acidifiers use to be inorganic chemicals that either produce or become acid. Suitable examples are: Ammonium chloride, calcium chloride.

In the scope of the present application it is understood that any indicated percent range or listed substance can be freely combined with the methods of the invention, as far as this is reasonable for the pursued purpose and does not exceed the scope of the main claim.

EXAMPLES

In the ensuing examples the relative quantities of the solubilizing agents can be changed inside the margins indicated for each component in the method according to the invention. The addition of glyceryl oleate and tocopherol is optional.

The resulting solubilisate can be diluted with an aqueous solution in order to obtain a finished solution. The volume of the aqueous solution can vary according to the desired volume of the finished solution.

It is possible to upscale or downscale the indicated amounts according to the desired absolute amount of the agent to be solubilized in the solubilisate. The solubilisate can be portioned according to the desired final amount of the agent that shall be administered to a patient in need thereof or consumed by a dietary supplement user.

In general, the produced solubilisates produced according to the method of the invention had a specific gravity of 0.92-0.94.

Standard chemicals were purchased from Sigma-Aldrich, Darmstadt, Germany.

Example 1: Solubilization of Azithromycin

Azithromycin is a broad-spectrum antibiotic that is widely used against infections by some Gram-positive, some Gram-negative and many atypical bacteria. Azithromycin belongs to BCS Class 4 (low solubility—low permeability) pharmaceuticals.

Ca. 10 ml of a solubilisate of azithromycin were generated by the following procedure: 200 mg azithromycin (Sigma-Aldrich, Darmstadt, Germany) were provided. 3.4 g 1-pamitoyl-2-oleoyl-sn-glycero-3-phosphocholine (POPC; Lipoid GmbH, Ludwigshafen, Germany), 5.5 ml MCT oil (Azelis, Moers, Germany), 320 mg L-alpha-lysophosphatidylcholine (Lipoid GmbH, Ludwigshafen, Germany), 300 µl ethanol, 110 µl oleic acid, 170 mg glyceryl stearate, 15 µl glyceryl oleate and 8 mg tocopherol were added under stirring for 5 min at room temperature (20±5° C.) and atmospheric pressure. Then the composition was cautiously heated under continued stirring, with an approximate temperature increment of 2° C./min. After ca. 8 min (ca. 36° C.) the composition started to become a clear solution. This solubilization process lasted for ca. 7 min more. Thus a solubilisate according to the invention was obtained after ca. 15 min at ca. 50° C. Then the heating and the stirring was stopped and the resulting solubilisate was allowed to cool down to room temperature. The solubilisate stayed clear and stable over min. 1 month.

Upon being diluted into an aqueous finished solution (2 ml solubilisate added to 100 ml bidest. water) under stirring the finished solution became quickly clear and had a slightly whitish appearance.

The bitter taste of azithromycin—which often causes a compliance problem, especially with children—could be covered by this solubilisate.

Example 2: Solubilization of Aciclovir

Aciclovir is an antiviral pharmaceutical agent. It is frequently used in the treatment of Herpes simplex infections, shingles and chickenpox. Aciclovir belongs to BCS Class 4 (low solubility—low permeability) pharmaceuticals.

Ca. 10 ml of a solubilisate of azithromycin were generated by the following procedure: 200 mg aciclovir (Sigma-Aldrich, Darmstadt, Germany) were provided. 5.7 g dimyristoyl phosphatidylcholine (DMPC; Lipoid GmbH, Ludwigshafen, Germany), 3.2 ml MCT oil (Azelis, Moers, Germany), 300 mg of a mixture of 1-lysophosphatidylcholine and 2-lysophosphatidylcholine (weight ratio: 1:1; Lipoid GmbH, Ludwigshafen, Germany), 250 µl ethanol, 120 µl oleic acid, 190 mg glyceryl stearate, 15 µl glyceryl oleate and 5 mg tocopherol were added under stirring for 5 min at room temperature (20±5° C.) and atmospheric pressure. Then the composition was cautiously heated under continued stirring, with an approximate temperature increment of 1° C./min. After ca. 45 min (ca. 65° C.) the composition started to become a clear solution. This solubilization process lasted for ca. 5 min more. Thus a solubilisate according to the invention was obtained after ca. 50 min at ca. 70° C. Then the heating and the stirring was stopped and the resulting solubilisate was allowed to cool down to room temperature. The solubilisate stayed clear and stable over min. 3 weeks.

Upon being diluted into an aqueous finished solution (2 ml solubilisate added to 100 ml bidest. water) under stirring the finished solution became quickly clear and had a slightly whitish appearance.

The taste of aciclovir—which patients often describe as unpleasant, sometimes also as metallic—could be covered by this solubilisate.

Example 3: Solubilization of Hydrochlorothiazide

Hydrochlorothiazide is a diuretic pharmaceutical agent. It is frequently used in the treatment of high blood pressure, swelling due to fluid build-up, diabetes insipidus, renal tubular acidosis and in the prophylaxis of persons with an elevated risk of kidneys stones. Hydrochlorothiazide belongs to BCS Class 4 (low solubility—low permeability) pharmaceuticals.

Ca. 10 ml of a solubilisate of hydrochlorothiazide were generated by the following procedure: 200 mg hydrochlorothiazide (Sigma-Aldrich, Darmstadt, Germany) were provided. 5 g of non-hydrogenated soy bean PC and POPC (weight ratio: 1:1; Lipoid GmbH, Ludwigshafen, Germany), 4 ml MCT oil (Azelis, Moers, Germany), 260 mg L-alpha-lysophosphatidylcholine (Lipoid GmbH, Ludwigshafen, Germany), 220 µl ethanol, 175 µl oleic acid, 190 mg glyceryl stearate and 20 µl glyceryl oleate were added under stirring for 5 min at room temperature (20±5° C.) and atmospheric pressure. Then the composition was cautiously heated under continued stirring, with an approximate temperature increment of 1° C./min. After ca. 38 min (ca. 58° C.) the composition started to become a clear solution. This solubilization process lasted for ca. 7 min more. Thus a solubilisate according to the invention was obtained after ca. 45 min at ca. 65° C. Then the heating and the stirring was stopped and the resulting solubilisate was allowed to cool down to room temperature. The solubilisate stayed clear and stable over min. 4 weeks.

Upon being diluted into an aqueous finished solution (2 ml solubilisate added to 100 ml bidest. water) under stirring the finished solution became quickly clear and had a slightly whitish appearance.

The taste of hydrochlorothiazide—which patients often describe as metallic—could be covered by this solubilisate.

Example 4: Solubilization of Coenzyme $Q_{10}$

Coenzyme $Q_{10}$ (synonyms: ubiquinone, ubidecarone, coenzyme Q, $CoQ_{10}$) is a ubiquitous coenzyme in most animals. Three redox states of coenzyme $Q_{10}$ have been described. The molecule acts as a two electron carrier and a one electron carrier, corresponding to its role in the electron transport chain and as a radical scavenger. Coenzyme $Q_{10}$ is hardly soluble in an aqueous environment and poorly absorbed in the body. However, it is a broadly marketed dietary supplement.

Ca. 10 ml of a solubilisate of coenzyme $Q_{10}$ were generated by the following procedure: 400 mg coenzyme $Q_{10}$ (Merck, Darmstadt, Germany) were provided. 2.6 g non-hydrogenated soy bean phosphatidylcholine (Lipoid GmbH, Ludwigshafen, Germany), 6.3 ml MCT oil (Azelis, Moers, Germany), 280 mg 2-lysophosphatidylcholine (Lipoid GmbH, Ludwigshafen, Germany), 180 µl ethanol, 90 µl oleic acid, 140 mg glyceryl stearate, 20 µl glyceryl oleate and 5 mg tocopherol were added under stirring for 5 min at room temperature (20±5° C.) and atmospheric pressure. Then the composition was cautiously heated under continued stirring, with an approximate temperature increment of 0.5° C./min. After ca. 36 min (ca. 38° C.) the composition started to become a clear solution. This solubilization process lasted for ca. 12 min more. Thus a solubilisate according to the invention was obtained after ca. 48 min at ca. 44° C. Then the heating and the stirring was stopped and the resulting solubilisate was allowed to cool down to room temperature. The color of the solubilisate was intense orange. The solubilisate stayed clear and stable over min. 2 months.

Upon being diluted into an aqueous finished solution (2 ml solubilisate added to 100 ml bidest. water) under stirring the finished solution became quickly clear and had a milky white yellowish appearance.

Example 5: Solubilization of Piperine

Piperine (IUPAC name: 1-[5-(1,3-benzodioxol-5-yl)-1-oxo-2,4-pentadienyl]piperidine) is the main alkaloid from Piper negrum (black pepper) and usually won by alcoholic extraction. It is a colorless to yellow solid at room temperature and poorly water-soluble. As many spicy substances piperine stimulates metabolism and gastrointestinal secretion, and it displays antimicrobial actions. Furthermore, it is a bioavailability enhancer. It was found to inhibit human CYP3A4 and P-glycoprotein, two enzymes involved in first-pass metabolism of xenobiotics. Thus, it can be used as a dietary supplement and/or as a bioavailability enhancer of other substances (mainly other dietary supplements).

Ca. 10 ml of a solubilisate of piperine were generated by the following procedure: 200 mg piperine extract (Sabinsa, Langen, Germany) were provided. 3.1 g 1,2-dioleyl-SN-glycero-3-phosphocholine (DOPC; Lipoid GmbH, Ludwigshafen, Germany), 5.8 ml MCT oil (Azelis, Moers, Germany), 300 mg 1-lysophosphatidylcholine (Lipoid GmbH, Ludwigshafen, Germany), 270 µl ethanol, 110 µl oleic acid, 170 mg glyceryl stearate, 15 µl glyceryl oleate and 8 mg tocopherol were added under stirring for 5 min at room temperature (20 t 5° C.) and atmospheric pressure. Then the composition was cautiously heated under continued stirring, with an approximate temperature increment of 1.5° C./min. After ca. 27 min (ca. 60° C.) the composition started to become a clear solution. This solubilization process lasted for ca. 16 min more. Thus a solubilisate according to the invention was obtained after ca. 43 min at ca. 85° C. Then the heating and the stirring was stopped and the resulting solubilisate was allowed to cool down to room temperature. The color of the solubilisate was intense yellow. The solubilisate stayed clear and stable over min. 12 months.

Upon being diluted into an aqueous finished solution (2 ml solubilisate added to 100 ml bidest. water) under stirring the finished solution became quickly clear and had a pale white appearance.

The characteristic poignant taste (more accurately, odor) of piperine could be covered by this solubilisate.

Example 6: Solubilization of Green Tea Extract

Green tea extract is produced from green tea leaves (*Camellia sinensis*). The main components are green tea catechins, such as epigallocatechin-3-gallate (EGCG), epicatechin (EC), epicatechin-3-gallate (ECg), epigallocatechin (EGC), catechin, and gallocatechin (GC), with EGCG being the most abundant of them in green tea extract. Green tea extract is often used as a dietary supplement, aiming at healthy effects attributed to catechins. They include above all antioxidant, anticarcinogenic, anti-inflammatory and anti-radiation actions. However, catechins, in particular EGCG, show a poor bioavailability and the solubility in water is rather limited.

Ca. 10 ml of a solubilisate of green tea extract were generated by the following procedure: 300 mg green tea extract (Sabinsa, Langen, Germany) were provided. 3 g phosphatidylcholine (PC and DMPC, weight ratio 1:1; Lipoid GmbH, Ludwigshafen, Germany), 5.9 ml MCT oil (Azelis, Moers, Germany), 280 mg 2-lysophosphatidylcholine (Lipoid GmbH, Ludwigshafen, Germany), 250 µl ethanol, 80 µl oleic acid, 160 mg glyceryl stearate, 20 µl glyceryl oleate and 14 mg tocopherol were added under stirring for 5 min at room temperature (20 t 5° C.) and atmospheric pressure. Then the composition was cautiously heated under continued stirring, with an approximate temperature increment of 2.5° C./min. After ca. 33 min (ca. 102° C.) the composition started to become a clear solution. This solubilization process lasted for ca. 4 min more. Thus a solubilisate according to the invention was obtained after ca. 36 min at ca. 110° C. Then the heating and the stirring was stopped and the resulting solubilisate was allowed to cool down to room temperature. The color of the solubilisate was dark brownish. The solubilisate stayed clear and stable over min. 16 months.

Upon being diluted into an aqueous finished solution (2 ml solubilisate added to 100 ml bidest. water) under stirring the finished solution became quickly clear and had a pale white brownish appearance.

The grassy (herbal) taste of diluted green tea extract could be covered by this solubilisate. This also holds true for the sometimes bitter taste of green tea, depending on the blend, which renders green tea unpopular for some people.

The invention claimed is:

1. A method for solubilizing a poorly water-soluble pharmaceutically active agent or dietary supplement, comprising the following steps:
   a) Providing one or more poorly water-soluble pharmaceutically active agents or dietary supplements in the range of 0.5 to 25 weight percent at room temperature and a pressure of 0.2 bar to 1 bar,
      wherein "poorly water-soluble" designates a pharmaceutically active agent or dietary supplement that requires more than 250 ml of aqueous media over the pH range of 1-7.5 for their highest dose to be dissolved;
   b) Adding in any sequence all the following solubilization agents to form a mixture:
      one or more phosphatidylcholines in the range of 20 to 80 weight percent,
      one or more medium-chain triglycerides in the range of 10 to 70 weight percent,
      one or more lysophosphatidylcholines in the range of 1 to 15 weight percent,
      one or more $C_2$ to $C_4$ alcohols in the range of 1 to 20 weight percent, and
      one or more saturated or unsaturated $C_{14}$ to $C_{20}$ fatty acids in the range of 0.5 to 10 weight percent,
      wherein the relative weight percentages of all ingredients add up to 100% and all solubilization agents are independently from one another a food additive, a pharmaceutically acceptable excipient, or both;
   c) Heating the resulting mixture by continuously increasing the temperature with a continuous temperature increment of 0.5° C./min to 3° C./min over a period of 20 to 60 minutes;
   d) Stopping the temperature increase in a temperature range of 30° C. to 125° C. as soon as a clear solution is reached to form a solubilisate; and
   e) Allowing a resulting solubilisate to cool down to room temperature.

2. The method according to claim 1, wherein said one or more saturated or unsaturated $C_{14}$ to $C_{20}$ fatty acids are oleic acid.

3. The method according to claim 1, wherein said one or more $C_2$ to $C_4$ alcohols are ethanol.

4. The method according to claim 1, wherein additionally in step b) one or more antioxidants in the overall range of 0.01 to 10 weight percent are added, said one or more antioxidants being a food additive, a pharmaceutically acceptable excipient, or both.

5. The method according to claim 4, wherein said one or more antioxidants are is ascorbyl palmitate, at least one tocopherol, or both.

6. The method according to claim 1, wherein the resulting solubilisate is used to mask a bitter or unpleasant taste and/or odor of the pharmaceutically active agent or dietary supplement.

7. The method according to claim 1, wherein said one or more saturated or unsaturated $C_{14}$ to $C_{20}$ fatty acids is glyceryl stearate.

* * * * *